| United States Patent [19]
Lunn

[11] 4,000,275
[45] Dec. 28, 1976

[54] IMMUNOSUPPRESSANTS

[75] Inventor: William H. W. Lunn, Indianapolis, Ind.

[73] Assignee: Eli Lilly and Company, Indianapolis, Ind.

[22] Filed: Feb. 9, 1972

[21] Appl. No.: 224,972

Related U.S. Application Data

[62] Division of Ser. No. 879,579, Nov. 24, 1969, Pat. No. 3,669,969.

[52] U.S. Cl. ............................................. 424/251
[51] Int. Cl.$^2$ .................................... A61K 31/505
[58] Field of Search ................................... 424/251

[56] References Cited
OTHER PUBLICATIONS

Camiener et al., *Progress in Drug Research*, vol. 16, pp. 113, 115, 116, 146, & 147.

*Primary Examiner*—Shep K. Rose
*Attorney, Agent, or Firm*—William B. Scanlon; Everet F. Smith

[57] ABSTRACT

Benzimidazo[2,1-b]quinazolin-12(6H)ones, immunosuppressives and agents for treatment of autoimmune diseases, are prepared via (1) reacting a 2-chlorobenzimidazole with an anthranilic acid or ester; (2) reacting a 2-aminobenzimidazole with an anthranilic acid or ester in the presence of trifluoroacetic acid or (3) reacting a 2-methylmercaptobenzimidazole with an anthraniloyl halide hydrohalide.

6 Claims, No Drawings

IMMUNOSUPPRESSANTS

BACKGROUND OF THE INVENTION

This is a division of Ser. No. 879,579 filed Nov. 24, 1969, now U.S. Pat. No. 3,669,969.

Recent advances in surgical medicine, particularly the accomplishments in human organ transplant operations, have been accompanied by an intensive search for agents to suppress the immune response mechanism. The immune response mechanism is triggered by the presence in the host body of a foreign substance known as an antigen. For example, the defense mechanism of the recipient of a transplanted organ such as a kidney or heart, responds to the newly acquired organ by seeking its removal from the host. In order to prevent rejection of the foreign organ, the host is treated with an immune suppressant prior to and after the transplant operation. In this manner the natural defense mechanism of the host is repressed until such time as the new organ is adopted by the host. One such commonly used immune suppressant is azathiaprene (U.S. Pat. No. 3,056,785).

Many disease conditions have been characterized as auto-immune diseases. For example, such diseases as the hemolytic anemias, Myasthenia gravis and rheumatoid arthritis have been described as auto-immune diseases in that such conditions are ascribed in part to the immune response mechanism. There exists a need for additional and more effective agents to inhibit or control the immune response mechanism and thereby provide a means for the treatment of auto-immune diseases. In addition, more effective immunosuppressive agents can play a major role in the success of surgical transplant operations.

DESCRIPTION OF THE PRIOR ART

Compounds possessing the tetracyclic, hetero-ring system containing three nitrogen atoms of the benzimidaz[2,1-b]-quinazolinone type are infrequently described in the literature; the only two references being those describing the synthesis of benzimidazo [2,1-b]quinazolin-12(6H)-one, [tetrahedron 21, 2179 (1965)], and the tetrahydro derivative, 1,2,3,4-tetrahydrobenzimidazo[2,1-b]quinazolin-12(6H)-one [J. Chem. Soc., 551 (1951)].

It is an object of this invention to provide a method for suppressing the immune response reaction in mammals. Another object of the present invention is to provide compositions for suppressing the immune response in mammals employing benzimidazo[2,1-b]quinazolin-12(6H)-ones. In particular it is an object of this invention to provide certain novel benzimidazo[2,1-b]-quinazolin-12(6H)-ones which are especially useful in suppressing the immune response mechanism in mammals.

SUMMARY

The compounds useful in the practice of this invention are represented by the following structural formula, with the indicated numbering system as employed herein:

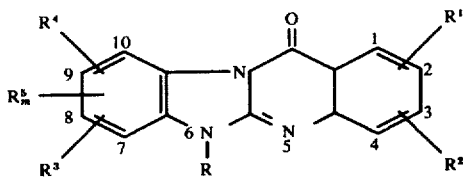

wherein $R^1$, $R^2$, $R^3$ and $R^4$ when taken separately are hydrogen, $C_1$ to $C_4$ lower alkyl, $C_1$ to $C_4$ lower alkoxy, halogen, nitro, amino, carbalkoxy or trifluoromethyl; and $R^1$ and $R^2$ or $R^3$ and $R^4$ when taken together with the adjacent benzene ring carbon atoms to which they are attached form a six-membered aromatic carbocyclic ring; $R^5$ represents methyl or chloro and m represents an integer of from 0 to 2, with the limitation that $R^3$ and $R^4$ being a moiety other than methyl or chloro m is 0; and wherein R is hydrogen, $C_1$ to $C_{12}$ alkyl, $C_3$ to $C_5$ alkenyl, $C_3$ to $C_5$ epoxyalkyl, $C_2$ to $C_{18}$ alkanoyl, benzyl, $C_4$ to $C_{11}$ cycloalkanoyl, $C_8$ to $C_{13}$ bicycloalkanoyl, $C_8$ to $C_{13}$ bicycloalkenoyl, $-[CH_2]_p-Z$ wherein p is an integer from 1 to 4 and Z is lower alkoxy, carboxy, carbalkoxy, or di-lower alkylamino, or a group of the formula

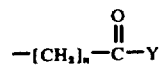

wherein n is an integer of from 0 to 4 and Y is carboxy lower alkyl, carbalkoxy lower alkyl, phenyl, naphthyl, phenyl substituted by lower alkyl, lower alkoxy, halogen, nitro, amino, trifluoromethyl, carboxy or carbalkoxy, or naphthyl substituted by lower alkoxy, halogen, nitro, amino, carboxy or carbalkoxy, with the limitation that when Y is carboxy lower alkyl or carbalkoxy lower alkyl n is 0 or 1 and Y is naphthyl or substituted naphthyl n is 0.

The compounds described herein are prepared generally by the reaction of a 2-chlorobenzimidazole with an anthranilic acid or ester thereof. Where the desired substituted 2-chlorobenzimidazole is difficult to obtain, a 2-aminobenzimidazole, desirably substituted, is reacted with an anthranilic acid or ester in the presence of an acidic catalyst. Certain polyalkylated benzimidazo[2,1-b]quinazolin-12(6H)ones, such as the tri- or tetra-methylated compounds are best synthesized by the novel reaction of a desirably alkylated 2-methylmercaptobenzimidazole with an anthraniloyl halide hydrohalide.

The benzimidazo[2,1-b]quinazolin-12(6H)ones prepared by the above described methods undergo N-alkylation and N-acylation predominantly at the nitrogen in the 6-position.

The compounds of the present invention are useful as immunosuppressant agents.

DETAILED DESCRIPTION

As previously described the compounds of the present invention are represented by the following general formula:

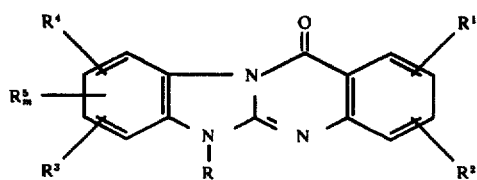

wherein $R^1$, $R^2$, $R^3$ and $R^4$ when taken separately are hydrogen, $C_1$ to $C_4$ lower alkyl, $C_1$ to $C_4$ lower alkoxy, halogen, amino, nitro, carbalkoxy, or trifluoromethyl; and $R^1$ and $R^2$ or $R^3$ and $R^4$ when taken together with the adjacent benzene ring carbon atoms to which they are attached form a six-membered aromatic carbocyclic ring; $R^5$ represents methyl or chloro and m represents an integer of from 0 to 2, with the limitation that $R^3$ and $R^4$ being a moiety other than methyl or chloro m is 0; and wherein R is hydrogen, $C_1$ to $C_{12}$ alkyl, $C_3$ to $C_5$ alkenyl, $C_3$ to $C_5$ epoxyalkyl, $C_2$ to $C_{16}$ alkanoyl, benzyl, $C_4$ to $C_{11}$ cycloalkanoyl, $C_8$ to $C_{13}$ bicycloalkanoyl, $C_8$ to $C_{13}$ bicycloalkenoyl, $-[CH_2]_p-Z$ wherein p is an integer from 1 to 4 and Z is lower alkoxy, carboxy, carbalkoxy, or di-lower alkylamino, or a group of the formula

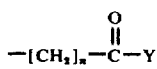

wherein n is an integer of from 0 to 4 and Y is carboxy lower alkyl, carbalkoxy lower alkyl, phenyl, naphthyl, or phenyl substituted by lower alkyl, lower alkoxy, halogen, nitro, amino, trifluoromethyl, carboxy or carbalkoxy, or naphthyl substituted by lower alkoxy, halogen, nitro, amino, carboxy or carbalkoxy, with the limitation that when Y is carboxy lower alkyl or carbalkoxy lower alkyl n is 0 or 1 and when Y is naphthyl or substituted naphthyl n is 0.

The term "lower alkyl" as employed herein refers to methyl, ethyl, n-propyl, isopropyl, n-butyl, isobutyl, secbutyl and t-butyl. "Lower alkoxy" refers to methoxy, ethoxy, n-propoxy, isopropoxy, and sec-butoxy. "Halogen" refers to fluoro, chloro, bromo and iodo. The term "carbalkoxy" refers to the esters of the carboxylic acid function formed with the lower alcohols such as methanol, ethanol, isopropanol, n-butanol and the like.

When in the above formula R is $C_1$ to $C_{12}$ alkyl R can be a straight or branched carbon chain such as methyl, ethyl, n-propyl, isopropyl, n-butyl, isobutyl, n-pentyl, n-hexyl, n-heptyl, n-octyl, isooctyl, n-nonyl, n-decyl, 3-methylnonyl, n-undecyl, n-dodecyl and the like. When R is $C_3$ to $C_5$ alkenyl R can be allyl, 2-butenyl, 3-butenyl, 2-pentenyl, 4-pentenyl an like unsaturated radicals. When R is $C_3$ to $C_5$ epoxyalkyl, R can be 2,3-epoxypropyl, 2,3-epoxybutyl, 3,4-epoxybutyl, 2,3-epoxypentyl, 3,4-epoxypentyl and the like. When R is $C_2$–$C_{16}$ alkanoyl R can be acetyl, propionyl, butyryl, isobutyryl, valeryl, isovaleryl, caproyl, heptanoyl, caprylyl, pelargonoyl, decanoyl (capryl), hendecanoyl, lauroyl, myristoyl, palmitoyl, and the like. When R is $C_4$ to $C_{11}$ cycloalkanoyl R can be cyclopropanoyl, cyclobutanoyl, cyclopentanoyl, cyclohexanoyl, 4-methylcyclohexanoyl, 4-isopropylhexanoyl, cycloheptanoyl, 3-methylcycloheptanoyl, cyclooctanoyl, 3-ethylcyclooctanoyl and the like. When R is $C_8$–$C_{13}$ bicycloalkanoyl R can be bicyclo [2.2.1]heptan-2-oyl, bicyclo[2.2.2]octan-2-oyl, 1,7,7-trimethylbicyclo[2.2.1]heptan-3-oyl, dimethyladamantoyl, bicyclo[5.3.0]dodecanoyl and the like, and when R is $C_8$–$C_{13}$ bicycloalkenoyl, R can be bicyclo[2.2.1] heptenoyl, bicyclo[3.3.0]octenoyl, bicyclo[2.2.2]octenoyl, 5-methylbicyclo[5.3.0]decenoyl and the like.

When R is a group represented by the formula

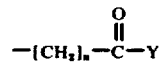

and Y is naphthyl or substituted naphthyl, and n is 0, R can be 1-naphthoyl, 2-naphthoyl, 2-amino-3-naphthoyl, 4-bromo-1-naphthoyl, 5-chloro-2-naphthoyl 3-nitro-1-napthoyl, 4-carboxynaphthoyl, 1-methoxy-2-naphthoyl, 2-ethoxy-6-naphthoyl, 4-carbomethoxy-1-naphthoyl, and the like; and when Y is carboxy lower alkyl n is 0 or 1, R can be carboxyacetyl, carboxypropionyl, carboxybutyryl, carboxyvaleryl, 2-oxo-3-carboxyacetyl, 2-oxo-4-carboxybutyl, 2-oxo-5-carboxypentyl, 2-oxo-6-carboxyhexyl, and the like, and when Y is carbalkoxy lower alkyl n is 0 or 1, R can be the esters of the above described carboxy lower alkyl substituent formed with the lower alcohols such as methanol, ethanol, propanol, butanol, isopropanol and the like; and when Y is phenyl or substituted phenyl n is an integer of from 0 to 4, illustrative of the groups representing R include the following: benzoyl, 4-methylbenzoyl, 2,4-dimethylbenzoyl, 2,4,6-trimethylbenzoyl, 3,5-dimethylbenzoyl, 4-chlorobenzoyl, 2,4-dichlorobenzoyl, 3,5-dichlorobenzoyl, 3-bromobenzoyl, 4-isopropylbenzoyl, 4-tert-butylbenzoyl, 4-nitrobenzoyl, 2-carbomethoxybenzoyl, 2-aminobenzoyl, anisoyl, 3-trifluoromethylbenzoyl, phenacyl, 4-bromophenacyl, 4-methylphenacyl, 2,4-dichlorophenacyl, 2-benzoylethyl, 2-(4-chlorobenzoyl)ethyl, 2-(2,4-dimethylbenzoyl)ethyl, 3-benzoylpropyl, 3-(4-trifluoromethylbenzoyl)ethyl, 4-benzoylbutyl, 4-(4-isopropylbenzoyl)butyl, and the like.

When in the foregoing formula R is $-[CH_2]_p-Z$ and p is an integer from 1 to 4 and Z is lower alkoxy R can be methoxymethyl, ethoxymethyl, 2-methoxyethyl, 3-methoxypropyl, 2-methoxypropyl; 4-isopropoxybutyl, 3-ethoxybutyl, n-butoxymethyl, and the like. When Z is carboxy R can be carboxymethyl, 2-carboxyethyl, 4-carboxybutyl, 3-carboxybutyl, 2carboxypropyl and the like. Similarly when Z is carbalkoxy, R can be carbomethoxymethyl, carboethoxymethyl, 2-carbomethoxyethyl, 3-carbomethoxypropyl, 4-carboethoxybutyl, carbopropoxymethyl and the like. When Z is di-lower alkyl amino R can be dimethylaminomethyl, diethylaminoethyl, di-n-propylaminomethyl, diethylaminoethyl, dimethylaminoethyl, di-n-butylaminopropyl, di-n-propylaminobutyl, dimethylaminopropyl, diethylaminopropyl, di-n-propylaminoethyl and the like and the salts thereof formed with pharmaceutically acceptable organic or inorganic acids.

When in the above formula $R^1$ and $R^2$ or $R^3$ and $R^4$ are taken together with the adjacent benzene ring carbon atoms to which they are attached to form a six-membered ring the compounds thus described as part of this invention include the following illustrative examples.

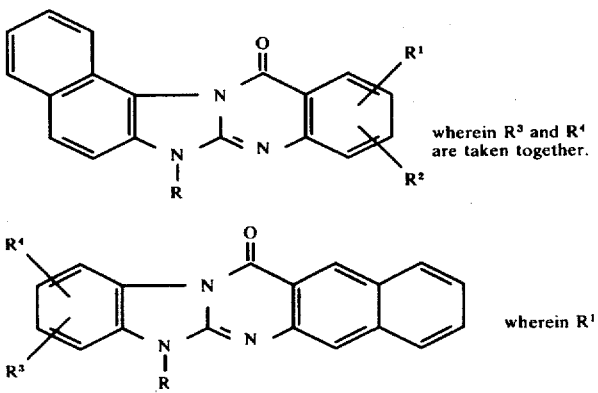

wherein R³ and R⁴ are taken together.

wherein R¹ and R² are taken together.

In the above examples R, R¹, R², R³ and R⁴ have the same meaning as previously defined.

The compounds described herein are formally named as benzimidazo[2,1-b]quinazolin-12(6H)ones but for the purposes of this description they are informally designated as azaquinazolinones.

The compounds of this invention are prepared by employing a variety of experimental methods. Generally, the azaquinazolinone or the substituted azaquinazolinone wherein R is hydrogen is prepared by the reaction of 2-chlorobenzimidazole or a substituted 2-chlorobenzimidazole with anthranilic acid or its ester or with substituted derivatives thereof. Alternatively, when the required substituted 2-chlorobenzimidazole is not readily available, the desired azaquinazolinone can be prepared by the novel reaction of a substituted 2-aminobenzimidazole with the appropriate anthranilic acid or ester.

The azaquinazolinones containing a nitro substituent in the 1, 2, 3 or 4 positions are preferably prepared by the reaction of 2-chlorobenzimidazole with a nitroanthraniloyl halide in the form of its hydrochloride salt.

The polyalkylated azaquinazolinones, for example 2, 8, 9-trimethylbenzimidazo[2,1-b]quinazolin-12(6H)one, are generally unobtainable by the above described general procedures. The polyalkylated azaquinazolinones described herein are synthesized by the novel reaction of an appropriately substituted 2-methylmercaptobenzimidazole with a substituted anthraniloyl chloride in the form of its hydrochloride salt.

The compounds wherein R is other than hydrogen are prepared by employing commonly known acylation and alkylation procedures on the previously prepared azaquinazolinone nucleus wherein R is hydrogen. Generally, the sodium salt of the azaquinazolinone is formed in a suitable inert solvent by reaction with sodium hydride. The hydrogen atom attached to the nitrogen in the 6-position of the azaquinazolinone nucleus is acidic in character and reacts with sodium hydride to form the anionic form of the azaquinazolinone. The sodium salt is then alkylated with an alkyl or substituted alkyl halide or acylated with an alkanoyl or aroyl halide to form the desired 6-substituted azaquinazolinone.

As previously mentioned, the azaquinazolinones of this invention are obtained by employing a variety of methods. In one such method briefly described above and designated herein as Method I, a 2-chlorobenzimidazole is reacted with an anthranilic acid or an ester thereof in a suitable unreactive solvent at a temperature sufficient to provide a convenient reaction rate. The 2-chlorobenzimidazole can be substituted at any of the available positions of the benzene ring. Among the substituted benzimidazoles which can be employed in the present reaction are 2-chloro-4-nitrobenzimidazole, 2-chloro-5-methylbenzimidazole, 2-chloro-6-methylbenzimidazole, 2,5-dichlorobenzimidazole, 6-bromo-2-chlorobenzimidazole, 2,5-dichloro-6-methylbenzimidazole, 2-chloro-5,6-dimethylbenzimidazole, 2-chloro-5-carboethoxybenzimidazole, 1H-naphth[2,3-d]imidazole, 1H-Naphth[1,2-d]-imidazole, 2,4,7-trichloro-5,6-dimethylbenzimidazole and the like. Likewise the anthranilic acid reactant can be substituted on the available positions of the benzene ring. For example, anthranilic acid, methyl anthranilate, methyl 4-methyl anthranilate, methyl 4-chloroanthranilate, methyl 5-iodoanthranilate, ethyl 4-nitroanthranilate and the like can be employed in preparing the compounds of the present invention. The corresponding substituted azaquinazolinone is obtained. Where, however, the benzimidazole moiety is mono substituted the possibility of obtaining mixtures of position isomers arises. This is because either of the imidazole nitrogen atoms can react with the ester or acid function of the anthranilic acid moiety and the position occupied by a single substituent in the azaquinazolinone product will depend upon which nitrogen is involved in the reaction. For example, the reaction of methyl anthranilate and 2-chloro-5-methylbenzimidazole affords a mixture of 8- and 9-methylazaquinazolinones.

The reaction can be carried out without the aid of a solvent by heating a mixture of the anthranilic acid ester with a 2-chlorobenzimidazole. It is desirable, however, to carry out the reaction in the presence of a suitable unreactive solvent, preferably diglyme. The 2-chlorobenzimidazole is dissolved or suspended in diglyme and a solution or suspension of the anthranilic acid ester in diglyme is added with stirring. The reaction mixture is then refluxed for periods of from 12 to 24 hours. The azaquinazolinone is precipitated from the reaction mixture by cooling and diluting with a large volume of cold water and is purified by recrystallization.

A second procedure employed in this invention for the preparation of the azaquinazoline nucleus involves the reaction of a 2-aminobenzimidazole with an anthranilic acid or ester thereof. This procedure is designated herein as Method II. As with the procedure of Method I, ring substituted 2-aminobenzimidazoles and substituted anthranilic acids and esters can be employed. According to this method, the 2-aminobenzimidazole and the anthranilic acid or ester are reacted in the presence of an acid catalyst, preferably trifluoroacetic acid, at a temperature between about 175° and 275° C. The preferred temperature range is between about 200° and 50° C. The acid catalyst is employed in an amount equal to at least one molar equivalent of the 2-aminobenzimidazole reactant. Generally, a slight excess of acid catalyst is preferred. The anthranilic acid reactant is used in amounts of about 0.1 to 0.2 moles in excess of the 2-aminobenzimidazole reactant.

In the absence of a solvent, the 2-aminobenzimidazole, anthranilic acid ester and trifluoroacetic acid mixture when heated from about 4 to about 8 hours affords the desired azaquinazolinone. In the presence of an inert solvent the reaction mixture is refluxed over a somewhat longer period of from about 12 to 24 hours to obtain the desired product.

The above described methods are illustrated in the following reaction scheme wherein A is hydrogen or lower alkyl and $R^1$, $R^2$, $R^3$, $R^4$ and $R_m^5$ have the same meaning as previously assigned.

reaction scheme $R^1$, $R^2$, $R^3$, or $R^4$ is an amino substituent, competing reactions can take place and result in unsatisfactory yields of the desired product. It should also be noted that when $R^1$ or $R^2$ is a nitro group, reaction with the 2-chlorobenzimidazole proceeds with difficulty; the method is, therefore, impractical for the synthesis of such nitro substituted azaquinazolinones.

The preferred manner of preparing a 2- or 4-nitrobenzimidazo[2,1-b]quinazolin-12(6H)one, designated herein as Method III, comprises reacting the required 2-chlorobenzimidazole with the nitroanthraniloyl chloride or bromide, as the hydrochloride or hydrobromide salt respectively, in an inert solvent such as benzene, toluene, xylene, or decalin at reflux temperature. The anthraniloyl halide salts formed with inorganic acids, such as hydrochloric or sulfuric acid, are suitable for use in this method, though generally the hydrochloride formed in making the acid chloride is used. The reaction mixture is usually refluxed for about 5 hours, although shorter periods of reflux can provide significant yields of the desired product. Method III can also be employed for the synthesis of azaquinazolinones wherein $R^1$, $R^2$, $R^3$, $R^4$ and $R_m^5$ represent other Reaction Scheme I

Method I

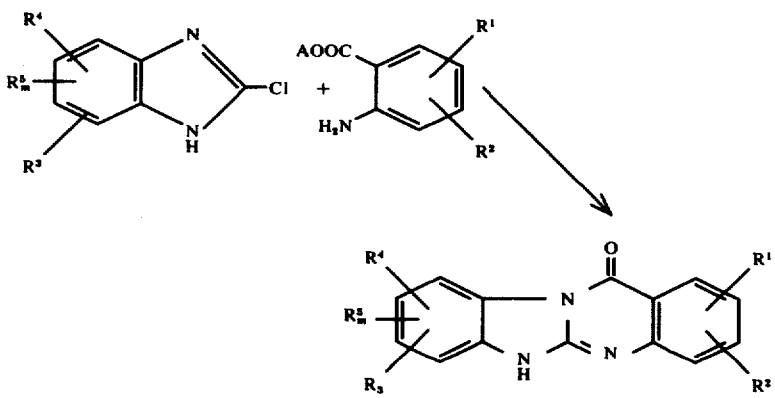

Method II

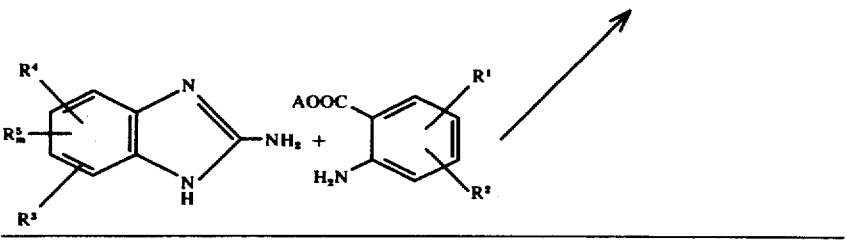

The preferred method for preparing the azaquinazolinones of this invention is Method I. This method appears to be the most generally applicable for the synthesis of a wide variety of substituted azaquinazolinones and is usually the method of choice unless the requisite 2-chlorobenzimidazole starting material is very difficult to obtain. When in the above substituent groups, as previously defined, but it is particularly useful for preparing the nitroazaquinazolinones.

The following reaction scheme, wherein X is chloro or bromo, one or both of $R^1$ and $R^2$ are nitro and $R^3$, $R^4$ and $R_m^5$ have the same meaning as previously assigned, is illustrative of Method III:

Reaction Scheme II

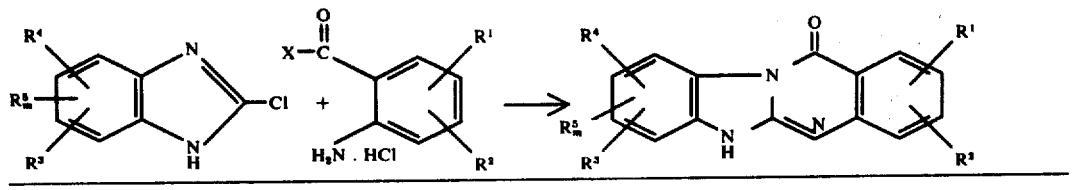

The nitroazaquinazolinones obtained by the procedure of Method III can be reduced by well-known catalytic reduction procedures to provide the corresponding aminoazaquinazolinones.

Certain of the azaquinazolinone compounds described herein containing multiple substituents, particularly the polymethyl substituted azaquinazolinones such as the 2,8,9-trimethyl and 3,8,9-trimethyl azaquinazolinones, are prepared by the reaction of a 2-methylmercaptobenzimidazole with an anthraniloyl halide hydrohalide salt. This novel method for the preparation of azaquinazolinones, designated herein as method IV is illustrated by the following Reaction Scheme III.

ence of sodium hydroxide to yield the 2-mercaptobenzimidazole which is methylated with methyl iodide in the presence of sodium hydroxide.

The anthraniloyl halide hydrohalide, employed in Method III for the preparation of nitroazaquinazolinones and in Method IV for the preparation of the polysubstituted azaquinazolinones, is preferably the anthraniloyl chloride hydrochloride, conveniently formed by the reaction of the anthranilic acid with thionyl chloride. Although the anthraniloyl chloride hydrochloride can be isolated and purified prior to use as a reactant, it is conveniently employed in less pure form as obtained directly from the reaction mixture in which it is formed. After evaporation of excess thionyl Reaction Scheme III

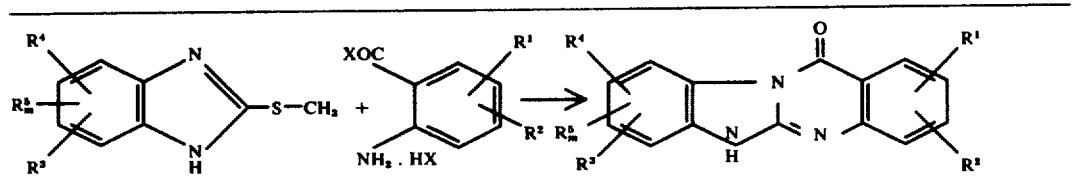

In the above formula X is Cl or Br and $R^1$, $R^2$, $R^3$, $R^4$ and $R_m{}^5$ have the same meaning as previously assigned. The reaction is carried out by adding the anthraniloyl halide hydrohalide, preferably the anthraniloyl chloride hydrochloride, in dry toluene to a solution of the appropriately substituted 2-methylmercaptobenzimidazole in dry pyridine. The reaction mixture is initially stirred at ambient temperature for about two hours and then diluted with dry dimethylformamide and stirred under reflux for about five hours. The azaquinazolinone reaction product is generally recovered from the reaction mixture
by evaporating the mixture and fractionally crystallizeing the solid residue from an appropriate solvent.

As indicated, the reaction is carried out in two stages. Initially, the reaction is carried out at room temperature under mild acylation conditions in a basic solvent combination, preferably toluene and pyridine. Following the initial reaction, during which a preponderance of a single intermediate is formed as indicated by thin layer chromatography, the reaction mixture is heated to a temperature between about 150° and 250° C. to complete the reaction. The increase in temperature is accomplished by adding to the initial reaction mixture a dry high boiling solvent such as dimethylformamide and heating the mixture to the reflux temperature.

The reaction is particularly useful for the preparation of the polymethylated azaquinazolinones, some of which are not conveniently synthesized by the previously described Methods I and III. The required substituted 2-methylmercaptobenzimidazole is prepared by the reaction of the appropriately substituted o-phenylenediamine with carbon disulfide in the preschloride and hydrogen chloride from the reaction mixture, the product residue is used directly as a reactant for the preparation of the desired azaquinazolinone.

Generally the starting materials used in this description are obtained from commercial sources or are synthesized by methods well known to those skilled in the art. For example, the 2-chlorobenzimidazoles are prepared by the chlorination of 2-hydroxybenzimidazoles with phosphorous oxychloride. 2-Aminobenzimidazoles are prepared by the reaction of an o-phenylenediamine with cyanogen bromide. For the preparation of certain 2-chlorobenzimidazoles not readily obtainable by customary procedures, an alternative procedure was employed. In this procedure, a desirably substituted 2-mercaptobenzimidazole suspended in a solution of methanol and concentrated hydrochloric acid is reacted with chlorine by bubbling the gas through the solution. The temperature of the reaction mixture is maintained at about 25° to 30° C. Passage of chlorine is continued for about 30 minutes, the methanol removed by evaporation and the pH adjusted to about pH 8 with ammonium hydroxide. The product a 2-chlorobenzimidazole precipitates and is purified by recrystallization. When 2-mercapto-5,6-dimethylbenzimidazole is subjected to the above preparative method with slight modifications, the novel intermediate 2,4,7-trichloro-5,6-dimethylbenzimidazole is obtained thereby.

The azaquinazolinones prepared by any of the above described methods undergo alkylation and acylation substitution reactions in which the hydrogen attached to the nitrogen in the six position is replaced. Conventional methods of alkylation and acylation can be employed. Alkylation or acylation can occur at either the 5- or 6-position, though generally the 6-substituted product proved to be the preponderant isomer. In those instances where mixtures of both 5- and 6-substituted products are formed, the isomers can be separated by careful fractional recrystallization from appropriate solvents. It is possible to differentiate between the 5- and 6-substituted products on the basis of their spectral characteristics.

The alkylation of the azaquinazolinones described herein, where R is hydrogen, is carried out by the reaction with sodium, or preferably sodium hydride, in anhydrous dimethylformamide to form the sodio derivative which is then reacted with the appropriate alkyl, alkenyl or epoxyalkyl halide. The sodio derivative imparts a characteristic yellow color to the dimethylformamide solution. On reaction with the alkylating agent, the yellow color gradually fades and disappears. When in the above general formula

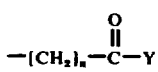

and n is an integer of from 1 to 4 or

the corresponding halides

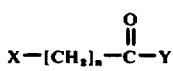

and

wherein X is chloro, bromo or iodo, comprise the alkylating agent.

An alternative method of alkylation comprises reacting the azaquinazolinone with a dialkyl ester of sulfuric acid such as dimethyl sulfate and diethyl sulfate. This method can be employed to advantage for the synthesis of compounds wherein R is lower alkyl, for example, methyl, ethyl or propyl.

Acylation of the azaquinazolinones is generally carried out by employing conventional procedures. For example, the sodio derivative of azaquinazolinone can be reacted with an alkanoyl halide to obtain the desired 6-acylated product. When R is

and n is 0 the corresponding halides

wherein X is chloro or bromo comprise the acylating agent. For example, when n = 0, and Y is phenyl or substituted phenyl and X is chloro, the acylating agent is benzoyl chloride or a substituted benzoyl chloride. The preferred solvent, and the one most generally applicable for the acylation of the sodium salt of the azaquinazolinones, is dimethylformamide. However, certain acylated azaquinazolinones are best prepared by employing other solvents such as tetrahydrofuran. For example, in the case of acylation with 2,4,6-trimethylbenzoyl chloride it is necessary to make and react the sodium salt of the azaquinazolinone in tetrahydrofuran rather than dimethylformamide. When the latter solvent is employed a quantitative recovery of unacylated starting material is obtained.

As previously noted, the compounds of this invention are useful in suppressing the immune reaction in mammals. The compounds can be classed as "immunosuppressant agents", by which is meant agents which suppress the formation of antibodies to foreign substances. The activity of the compounds of this invention can also be characterized as anti-allergic activity in that the allergic reaction is part of the immune reaction against foreign antigens. Such anti-allergic activity differs from the well-known anti-histamine activity.

The ability of compounds of this invention to suppress the immune reaction in a host animal was measured by their activity as anti-allergic agents in the following described test. The test procedure is essentially that described by H. C. Nathan et al. *Proc. Soc. Exptl. Biol. Med.* 107, 796(1961).

Although immune suppressant activity was determined in mice using sheep erythrocytes as the antigen (foreign protein), it should be recognized that similar activity would be demonstrated against any foreign protein (antigen) in any mammal.

Groups of five 20 g. male Swiss mice are injected intraperitoneally with 0.2 ml. of a 1–80 suspension of washed sheep red blood cells (approximately $5 \times 10^7$ cells/mouse). Forty-eight hours before and 48 hours after the red blood cell injections, the test compounds are administered intraperitoneally in various dosages to various animal groups. Seven days after the red blood cell antigen injections, the mice are bled by cardiac puncture and the sera from each group of five mice is pooled. Antibody determinations are made on the serum pools by a hemagglutination pattern procedure, in which 2-fold serum dilutions are mixed with equal volumes of one percent suspensions of sheep red blood cells in plastic depression trays, which are then incubated for 4 hours at 37° C., and assessed for hemagglutinin content. Comparisons between serum pools from treated and control groups are made, and 75 percent (4-fold) or greater suppression of hemagglutinin in treated groups is considered significant and is the basis for the stated activities of the test compounds.

The following tables list the activities of representative compounds of the invention. The activity is expressed in terms of the dose, in mg. per kg., which was found to give at least a 75 percent (4-fold) or greater antibody suppression in the above described test. Table I includes azaquinazolinones unsubstituted at the 6-position. Table II includes 6-alkyl, 6-alkenyl, 6-alkanoyl, 6-epoxyalkyl, and 6-bicycloalkenoyl-substituted azaquinazolinones. Table III lists exemplary compounds of the invention wherein the 6-substituent is represented by the formula

and Y is phenyl. Table IV lists exemplary 6-substituted azaquinazolinones wherein the substituent group R is represented by the formula

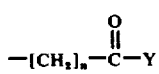

and Y is carbalkoxy lower alkyl. Table V includes 6-substituted azaquinazolinones wherein the substituent group R is represented by the formula

and Z is lower alkoxy, di-lower alkylamino, carboxy or carbalkoxy.

TABLE I

Benzimidazo[2,1-b]quinazolin-12(6H)ones

| Compound Name | Activity mg./kg,i.p. |
|---|---|
| Benzimidazo[2,1-b]quinazolin-12(6H)one | 6.2 |
| 3-Methylbenzimidazo[2,1-b]quinazolin-12(6H)one | 0.4 |
| 8,9-Dimethylbenzimidazo[2,1-b]quinazolin-12(6H)one | 0.2 |
| 3,8,9-Trimethylbenzimidazo[2,1-b]quinazolin-12(6H)one | 12.5 |
| 2,8,9-Trimethylbenzimidazo[2,1-b]quinazolin-12(6H)one | 0.8 |
| 8-Methylbenzimidazo[2,1-b]quinazolin-12(6H)one and 9-methylbenzimidazo[2,1-b]quinazolin-12(6H)one (mixture) | 50 |
| 2-Iodobenzimidazo[2,1-b]quinazolin-12(6H)one | 1.6 |
| 8-Chlorobenzimidazo[2,1-b]quinazolin-12(6H)one and 9-chlorobenzimidazo[2,1-b]quinazolin-12(6H)one (mixture) | 12.5 |
| 3-Nitrobenzimidazo[2,1-b]quinazolin-12(6H)one | 25 |
| Naphth[1',2':4,5]imidazo[2,1-b]quinazolin-8(14H)one | 3.1 |
| Naphth[2',3':5,6]pyrimido[3,2-a]benzimidazo-13(5H)one | 0.1 |
| 7,10-Dichloro-8,9-dimethylbenzimidazo-[2,1-b]quinazolin-12(6H)one | 12.5 |
| 7,10-Dichloro-3,8,9-trimethylbenzimidazo-[2,1-b]quinazolin-12(6H)one | 0.4 |

TABLE II

6-Substituted benzimidazo[2,1-b]quinazolin-12(6H)ones (R is alkyl, alkenyl, alkanoyl)

| Compound Name | Activity mg/kg,i.p. |
|---|---|
| 6-Methylbenzimidazo[2,1-b]quinazolin-12(6H)one | 0.4 |
| 6,8,9-Trimethylbenzimidazo[2,1-b]quinazolin-12(6H)one | 0.2 |
| 2,6,8,9-Tetramethylbenzimidazo[2,1-b]quinazolin-12(6H)one | 12.5 |
| 6-Ethylbenzimidazo[2,1-b]quinazolin-12(6H)one | 3.1 |
| 6-Isopropylbenzimidazo[2,1-b]quinazolin-12(6H)one | 3.1 |
| 6-n-Amylbenzimidazo[2,1-b]quinazolin-12(6H)one | 3.1 |
| 6-n-Nonylbenzimidazo[2,1-b]quinazolin-12(6H)one | 12.5 |
| 6-Allylbenzimidazo[2,1-b]quinazolin-12(6H)one and minor amount of 5-allylbenzimidazo[2,1-b]quinazolin-12(6H)one (mixture) | 6.2 |
| 6-Palmitoylbenzimidazo[2,1-b]quinazolin-12(6H)one | 0.2 |
| 6-(2-Norbornen-5-ylcarbonyl)benzimidazo[2,1-b]quinazolin-12(6H)one | 25 |
| 6-(2,3-Epoxypropyl)benzimidazo[2,1-b]quinazolin-12(6H)one | 50 |

TABLE III

6-Substituted benzimidazo[2,1-b]quinazolin-12(6H)ones (R is —[CH$_2$]$_n$—C(=O)—Y, Y is phenyl and substituted phenyl)

| Compound Name | Activity mg/kg,i.p. |
|---|---|
| 6-Benzoylbenzimidazo[2,1-b]quinazolin-12(6H)one | 0.8 |
| 6-(2-Chlorobenzoyl)benzimidazo[2,1-b]quinazolin-12(6H)one | 3.1 |
| 6-(2-Carbomethoxybenzoyl)benzimidazo[2,1-b]quinazolin-12(6H)one | 6.2 |
| 6-(2,4-Dichlorobenzoyl)benzimidazo[2,1-b]quinazolin-12(6H)one | 0.4 |
| 6-(2,4-Dimethylbenzoyl)benzimidazo[2,1-b]quinazolin-12(6H)one | 0.2 |
| 6-(3,5-Dimethylbenzoyl)benzimidazo[2,1-b]quinazolin-12(6H)one | 1.6 |
| 6-(2,4,6-Trimethylbenzoyl)benzimidazo[2,1-b]quinazolin-12(6H)one | 3.1 |
| 6-(2,4-Dimethylbenzoyl)-3,8,9-trimethylbenzimidazo-[2,1-b]quinazolin-12(6H)one | 0.1 |
| 6-(2,4-Dimethylbenzoyl)-2,8,9-trimethylbenzimidazo-[2,1-b]quinazolin-12(6H)one | 0.4 |
| 6-Phenacylbenzimidazo[2,1-b]quinazolin-12(6H)one | 12.5 |

TABLE IV

6-Substituted benzimidazo[2,1-b]quinazolin-12(6H)ones (R is [CH$_2$]$_n$—C(=O)—Y, Y is carbalkoxy lower alkyl)

| Compound Name | Activity mg/kg,i.p. |
|---|---|
| 6-(4-Carbomethoxy-2-oxabutyl)benzimidazo[2,1-b]quinazolin-12(6H)one | 3.1 |
| 6-(3-Carbomethoxypropionyl)benzimidazo[2,1-b]quinazolin-12(6H)one | 25 |
| 6-(4-Carbomethoxybutyryl)benzimidazo[2,1-b]quinazolin-12(6H)one | 12.5 |

TABLE V

6-Substituted benzimidazo[2,1-b]quinazolin-12(6H)ones (R is —[CH$_2$]$_n$—Z)

| Compound Name | Activity mg/kg,i.p. |
|---|---|
| 6-Methoxymethylbenzimidazo[2,1-b]quinazolin-12(6H)-one | 50 |
| 6-(3-Dimethylaminopropyl)benzimidazo[2,1-b]quinazolin-12(6H)one | 25 |
| 6-(Carbethoxymethyl)benzimidazo[2,1-b]quinazolin-12-(6H)one | 50 |
| 6-(Carboxymethyl)benzimidazo[2,1-b]quinazolin-12(6H)-one | 12.5 |
| 6-(Carboxymethyl)benzimidazo[2,1-]quinazolin-12(6H)-one potassium salt. | 50 |
| 6-(4-Carbomethoxybutyl)benzimidazo[2,1-b]quinazolin-12(6H)one | 50 |
| 6-(4-Carboxybutyl)benzimidazo[2,1-b]quinazolin-12(6H)-one potassium salt | |

As demonstrated by the data presented in the foregoing tables, the compounds of this invention are highly effective immunosuppressants. Azathiaprene, the presently known immunosuppressant of choice, is effective at a dose of about 100 mg./kg. in suppressing the antibody response in the previously described test procedure.

When administered parenterally at a dose of from about 0.1 to about 100 mg./kg. of body weight, the compounds of the present invention are effective in inhibiting the immune response mechanism. Although the in vivo mouse data presented above were obtained by intraperitoneal administration, the compounds can also be administered and are effective by the subcutaneous or intramuscular routes. Commonly employed pharmaceutical formulations for such parenteral routes can be used with the instant compounds. For example, when subcutaneous administration is the desired route, the compounds are suspended in their highly divided crystalline state in an inert diluent such as water. For intramuscular administration the compounds can be formulated with commonly employed excipients such as ethyl oleate, peanut oil, sesame oil or the like. The compounds can be administered on a daily single dose basis; however, it may be desirable to administer two or three smaller doses on a daily basis. In suitable cases, after the desired drug effect is observed following the initial daily dose regimen, less frequent administration, such as weekly or bi-weekly doses, may be found to be adequate.

In addition to their use in connection with organ transplantation, immunosuppressant agents are also useful in various diseases which have been in part ascribed to the immune response. Such diseases have been categorized as auto-immune diseases and include among others, hemolytic anemia, lupus erythematosus, lupus nephritis, lupoid hepatitis and rheumatoid arthritis.

In another of its aspects the present invention provides certain novel compounds which are especially useful in suppressing the immune response. Such compounds are represented by the following general formula:

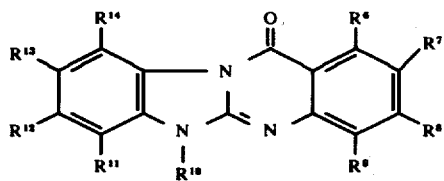

wherein $R^6$, $R^7$, $R^8$, $R^9$, $R^{11}$, $R^{12}$, $R^{13}$ and $R^{14}$ when taken separately are hydrogen, halogen, $C_1$ to $C_4$ alkoxy, nitro, amino, carbalkoxy or trifluoromethyl, and the adjacent R groups when taken together with the benzene ring carbon atoms to which they are attached form a six-membered aromatic carbocyclic ring; and wherein $R^{10}$ is hydrogen, $C_3$ to $C_5$ epoxyalkyl, —[$CH_2$-]$_p$—Z wherein p is an integer of from 1 to 4 and Z is lower alkoxy, carboxy, carbalkoxy or di-lower alkylamino, or a group of the formula:

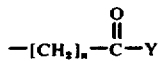

wherein n is an integer of from 0 to 4 and Y is carboxy lower alkyl, carbalkoxy lower alkyl, phenyl, naphthyl, phenyl substituted by lower alkyl, lower alkoxy, halogen, nitro, amino, trifluoromethyl, carboxy or carbalkoxy, or naphthyl substituted by lower alkoxy, halogen, nitro, amino, carboxy or carbalkoxy, with the limitations that when Y is carboxy lower alkyl or carbalkoxy lower alkyl, n is 0 or 1, and when Y is naphthyl or substituted naphthyl n is 0; provided that when $R^{10}$ is hydrogen at least one of $R^6$, $R^7$, $R^8$, $R^9$, $R^{11}$, $R^{12}$, $R^{13}$ and $R^{14}$ is a group other than hydrogen; and in addition, $R^8$ or $R^{10}$ is methyl, $R^{12}$ and $R^{13}$ are both methyl, $R^7$ is methyl when both $R^{12}$ and $R^{13}$ are methyl, and any of the groups $R^6$-$R^{14}$ is methyl when any other of $R^6$-$R^{14}$ is a group other than hydrogen or methyl.

Certain of the above defined novel compounds are highly effective in suppressing the immune response and are preferred compounds in the practice of the present invention. Among the preferred compounds are the following:

3-methylbenzimidazo[2,1-b]quinazolin-12(6H)one,
6-methylbenzimidazo[2,1-b]quinazolin-12-(6H)one,
8,9-dimethylbenzimidazo[2,1-b]quinazolin-12(6H)one,
6,8,9-trimethylbenzimidazo[2,1-b]quinazolin-12(6H)one,
2,8,9-trimethylbenzimidazo[2,1-b]quinazolin-12(6H)one,
7,10-dichloro-3,8,9-trimethylbenzimidazo[2,1-b]quinazolin-12(6H)one naphth[2',3':56-]pyrimido[3,2-a]benzimidazo-13(5H)one,
6-(2,4-dichlorobenzoyl)benzimidazo[2,1-b]quinazolin-12(6H)one,
6-(2,4-dimethylbenzoyl)benzimidazo[2,1-b]quinazolin-12(6H)one,
6-(3,5-dimethylbenzoyl)benzimidazo[2,1-b]quinazolin-12(6H)one,
6-(2,4-dimethylbenzoyl)-2,8,9-trimethylbenzimidazo[2,1-b]quinazolin-12(6H)one,
6-(2,4-dimethylbenzoyl)-3,8,9-trimethylbenzimidazo[2,1-b]quinazolin-12(6H)one.
6-benzoylbenzimidazo[2,1-b]quinazolin-12(6H)one The following illustrative examples more fully describe the present invention.

A. Preparation of Benzimidazo[2,1-b]quinazolin-12(6H)-ones.

Method I.

EXAMPLE 1

2-Chlorobenzimidazole, 4.58 g. (0.03 mole) and 2-amino-4-methylbenzoic acid, 4.9 g. (0.033 mole) were added to a 250 ml. flask containing 50 ml. of diglyme and the mixture was heated in an oil bath at a temperature of about 160° C. Solution occurred when the mixture became hot and, after 15 minutes at 160° C., a solid formed. The reaction mixture was cooled to room temperature, slurried with ice water and filtered. The crude solid product was recrystallized from dimethylformamide to yield 4.5 g. of white crystalline 3-methylbenzimidazo[2,1-b]quinazolin-12(6H)one melting at about 328°-335° C.

Elemental analysis of a sample dried at 120° gave the following results:
Calculated: C, 72.27; H, 4.45; N, 16.86.
Found: C, 72.03; H, 4.60; N, 16.80.

EXAMPLE 2

The reaction of 2-chloro-5,6-dimethylbenzimidazole with anthranilic acid according to the procedure described in Example 1 afforded 8,9-dimthylbenzimidazo[2,1-b]quinazolin-12(6H)one melting at about 300° C.

EXAMPLE 3

The reaction of 2-chlorobenzimidazole with 5-iodoanthranilic acid according to the procedure described in Example 1 yielded 2-iodobenzimidazo[2,1-b]quinazolin-12(6H)one melting at about 372° C.

EXAMPLE 4

The reaction of 2-chloro-5-methylbenzimidazole with anthranilic acid according to the procedure described in Example 1 yielded a solid mixture comprising 8-methylbenzimidazo[2,1-b]-quinazolin-12(6H)one and 9-methylbenzimidazo[2,1-b]quinazolin-12(6H)one.

EXAMPLE 5

The reaction of 2,5-dichlorobenzimidazole with anthranilic acid following the procedure described in Example 1 afforded a solid mixture of 8-chlorobenzimidazo[2,1-b]quinazolin-12(6H)one and 9-chlorobenzimidazo [2,1-b]quinazolin-12(6H)one.

EXAMPLE 6

2-Chlorobenzimidazole, 15 g., was dissolved in 300 ml. of diglyme and methyl anthranilate, 14.7 g., was added. The mixture was refluxed with stirring for about 22 hours, cooled to room temperature and then poured into 1500 ml. of cold water. The solid precipitate which formed was filtered and washed with water. The crude product, benzimidazo[2,1-b]quinazolin-12(6H)one, after recrystallization from dimethylformamide, melted at about 365°–370° C.

EXAMPLE 7

Preparation of 2,4,7-trichloro-5,6-dimethylbenzimidazole.

Ten grams (0.56 mole) of 2-mercapto-5,6-dimethylbenzimidazole was suspended in a solution of 100 ml. of methanol and 200 ml. of concentrated hydrochloric acid. Chlorine was bubbled through the suspension while the temperature was maintained at about 25° to 30° C. by means of an ice bath. The chlorine saturated suspension was then warmed to a temperature of about 45° C. and after about 10 minutes a homogenous solution was formed. This solution was stirred at a temperature of about 45° C. for ten minutes and cooled to room temperature. A heavy precipitate was formed and the reaction mixture was diluted with 200 ml. of water. The pH of the mixture was adjusted to a pH of about 8 by the addition of ammonium hydroxide. The precipitate was filtered, washed with water and crystallized from ethanol-water to yield 2,4,7-trichloro-5,6-dimethylbenzimidazole melting at about 280°–285° C.

EXAMPLE 8

Preparation of 7,10-dichloro-8,9-dimethylbenzimidazo[2,1-b]quinazolin-12(6H)one.

2,4,7-Trichloro-5,6-dimethylbenzimidazole, 3.13 g. and methyl anthranilate, 1.9 g. were dissolved in 50 ml. of diglyme and the solution was refluxed for 16 hours. On cooling a precipitate was formed and filtered to yield one gram of 7,10-dichloro-8,9-dimethylbenzimidazo[2,1-b]quinazolin-12-(6H) one melting above 300° C.

Analysis: Calculated: C, 57.85; H, 3.34; N, 12.65; Cl, 21.35. Found: C, 58.06; H, 3.60; N, 12.72; Cl, 21.06.

EXAMPLE 9

Preparation of 7,10-dichloro-3,8,9-trimethylbenzimidazo[2,1-b]quinazolin-12(6H)one 2,4,7-Trichloro-5,6-dimethylbenzimidazole, 3 g. (.012 mole) and 2-amino-4-methylbenzoic acid, 1.8 g. (0.012 mole) were added to 30 ml. of diglyme and the mixture refluxed overnight with continual stirring. The reaction mixture was cooled to room temperature and 30 ml. of ether added. The brown precipitate which was formed was filtered and washed with ether and recrystallized from dimethylformamide to yield 550 mg. of 7,10-dichloro-3,8,9-trimethylbenzimidazo[2,1-b]quinazolin-12(6H)one melting above 330° C.

Analysis: Calculated, C, 58.97; H, 3,78; N, 12.14; Cl, 20.48. Found: C, 59.03; H, 3.92; N, 12.17; Cl, 20.38.

EXAMPLE 10

Following the procedure described in Example 1, the following compounds are prepared from the indicated reactants:

3-Chlorobenzimidazo[2,1-b]quinazolin-12(6H)one is prepared with 2-chlorobenzimidazole and 4-chloroanthranilic acid.

2-Chlorobenzimidazo[2,1-b]quinazolin-12(6H)one is prepared with 2-chlorobenzimidazole and 5-chloroanthranilic acid.

2-Methylbenzimidazo]2,1-b]quinazolin-12(6H)one is prepared with 2-chlorobenzimidazole and 5-methylanthranilic acid.

4-Methylbenzimidazo[2,1-b]quinazolin-12(6H)one is prepared with 2-chlorobenzamidazole and 3-methylanthranilic acid.

4,8,9-Trimethylbenzimidazo[2,1-b]quinazolin-12(6H)one is prepared with 2-chloro-5,6-dimethylbenzimidazole and 3-methylanthranilic acid.

3-Chloro-8,9-dimethylbenzimidazo[2,1-b]quinazolin-12(6H)-one is prepared with 2-chloro-5,6-dimethylbenzimidazole and 4-chloroanthranilic acid.

2-Bromo-8,9-dimethylbenzimidazo[2,1-b]quinazolin-12(6H)-one is prepared with 2-chloro-5,6-dimethylbenzimidazole and 5-bromoanthranilic acid.

3-Trifluoromethylbenzimidazo[2,1-b]quinazolin-12(6H)one is prepared with 2-chlorobenzimidazole and 4-trifluoromethyl-anthranilic acid.

3-Trifluoromethyl-8,9-dimethylbenzimidazo[2,1-b]quinazolin-12(6H)one is prepared with 2-chloro-5,6-dimethylbenzimidazole and 4-trifluoromethylanthranilic acid.

3-Ethoxybenzimidazo[2,1-b]quinazolin-12(6H)one is prepared with 2-chlorobenzimidazole and 4-ethoxyanthranilic acid.

Preparation of benzimidazo[2,1-b]-quinazolin-12(6H)ones

Method II

EXAMPLE 11

A mixture comprising 2-amino-5,6-dimethylbenzimidazole, 3.2 g. (0.02 mole); methyl anthranilate, 3.9 ml. (0.03 mole) and trifluoroacetic acid 1.48 ml. (0.02 mole) was heated at a temperature of about 225° C. for 6 hours under reflux conditons. The reaction mixture was cooled and the oily product was slurried in chloroform to precipitate solid product. The solid product was filtered and washed with water to yield 0.47 g. of 8,9-dimethylbenzimidazo[2,1-b]quinazolin-12(6H)one melting at about 300° C. to 330° C. with decomposition after recrystallization from dimethylformamide-water. elemental analysis of a sample dried at 120° C. gave the following results.

Calculated: C, 72.98; H, 4.98; N, 15.96. Found: C, 72.96; H, 5.22; N, 15.68.

EXAMPLE 12

Following the procedure described in Example 11, the following compounds can be prepared with the indicated starting materials;

A mixture of 8-methyl and 9-methylbenzimidazo[2,1-b]-quinazolin-12(6H)one is prepared from 2-amino-5-methylbenzimidazole and methylanthranilate.

A mixture of 8-chloro and 9-chlrobenzimidazo[2,1-b]-quinazolin-12(6H)one is prepared from 2-amino-5-chlorobenzimidazole and methylanthranilate.

Naphtho[1',2':4:5]imidazo[2,1-b]quinazolin-8-(14H)one is prepared from 2-aminonaphthol[1,2-d]imidazole and methylanthranilate.

Preparation of nitrobenzimidazo[2,1-b]quinazolin-12(6H)ones

Method III

EXAMPLE 13

2-Chlorobenzimidazole, 4.58 g. (0.03 mole), and 4 nitroanthraniloyl chloride as the hydrochloride salt, 7.17 g. were added to 150 ml. of dry benzene and the mixture was refluxed for five hours. The reaction solution was refrigerated and the precipitate was filtered to yield 10 g. of crude product, 3-nitrobenzimidazo[2,1-b]quinazolin-12(6H)one, which decomposed above 400° C. after recrystallization from dimethylformamide-water.

Analysis of a sample dried at 120° C. gave the following values.

Calculated: C, 60.00; H, 2.88; N, 19.99. Found: C, 59.76; H, 3.01; N, 20.09.

EXAMPLE 14

Following the procedure described in Example 13 the following nitrobenzimidazo [2,1-b]quinazolin-12(6H)ones can be prepared with the indicated starting materials:

2-Nitrobenzimidazo[2,1-b]quinazolin-12(6H)one, is prepared with 2-chlorobenzimidazole and 5-nitroanthraniloyl chloride hydrochloride.

3-Nitro-8,9-dichlorobenzimidazo[2,1-b]quinazolin-12(6H)-one is prepared with 2,5,6-trichlorobenzimidazole and 4-nitroanthraniloyl chloride hydrochloride.

Preparation of Benzimidazo[2,1-b]quinazolin-12(6H)ones

Method IV

EXAMPLE 15

2-Methylmercapto-5,6-dimethylbenzimidazole, 42.5 g. (0.22 mole), was stirred in 128 ml. of dry pyridine and 50 g. (0.24 mole) of 5-methylanthraniloyl chloride hydrochloride in 100 ml. of dry toluene was added slowly over a 30 minute period. The resulting mixture was stirred at room temperature for 2 hours, after which 720 ml. of dry dimethylformamide were added. The reaction mixture was then refluxed for 5 hours with stirring. The solid precipitate which formed during reflux was filtered, washed with dimethylformamide, and dried to yield 21 g. of 2,8,9-trimethylbenzimidazo[2,1-b]quinazolin-12(6H)one.

EXAMPLE 16

Following the procedure described in Example 15, 3,8,9-trimethylbenzimidazo[2,1-b]quinazolin-12(6H)one was prepared by the reaction of 2-methylmercapto-5,6-dimethylbenzimidazole with 4-methylanthraniloyl chloride hydrochloride. In this instance, the product failed to crystallize from the reaction mixture on reflux. Instead, the product was obtained by evaporating the reaction mixture to dryness, triturating the solid residue with dichloromethane, filtering the insoluble material and recrystallizing the solid material from dimethylformamide.

B. Preparation of 6-alkylated benzimidazo[2,1-b]quinazolin-12(6H)-ones

EXAMPLE 17

Benzimidazo[2,1-b]quinazolin-12(6H)one, 1.18 g. (0.005 mole) and 2 ml. of dimethyl sulfate were added to 50 ml. of dimethylformamide and heated with stirring at a temperature of 150°–155° C. for 20 hours in the presence of 0.5 ml. of pyridine. On cooling, the precipitated solid was filtered and recrystallized from dimethylformamide to yield 0.5 g. of 6-methylbenzimidazo[2,1-b]quinazolin-12(6H)one melting at about 267°–268.5° C. Elemental analysis of a sample of the above product dried at 120° C. gave the following results.

Calculated: C, 72.27; H, 4.45; N, 16.86. Found: C, 72.05; H, 4.50; N, 16.97.

EXAMPLE 18

To a vigorously stirred suspension of 1.18 g. (0.005 mole) of benzimidazo[2,1-b]quinazolin-12(6H)one in 50 ml. of dry dimethylformamide was added 0.23 g. of a suspension of sodium hydride in mineral oil (containing 58.8 percent sodium hydride). Stirring was continued for one hour to insure formation of the sodio derivative as indicated by dissolution of the azaquinazolinone with the formation of a yellow solution of the anion. To this solution, 1.24 ml. of n-amyl bromide were added and, after continuous agitation for four hours at ambient temperature, a precipitate formed. The reaction mixture was placed in the refrigerator overnight. The precipitate was removed by filtration and recrystallized from benzene to yield 350 mg. of 6-(n-pentyl)-benzimidazo[2,1-b]quinazolin-12(6H)one as white needles melting at about 186°–187.5° C. Elemental analysis of a sample of the crystalline product dried at 120° C. gave the following results.

Calculated: C, 74.73; H, 6.27; N, 13.76. Found: C, 74.79; H, 6.35; N, 13.82.

In an analogous manner the following compounds can be prepared by the reaction of the appropriate benzimidazo[2,1-b]-quinazolin-12(6H)one with the indicated alkylating agent:

6-Ethylbenzimidazo[2,1-b]quinazolin-12(6H)one is prepared with benzimidazo[2,1-b]quinazolin-12(6H)one and ethyl bromide.

6-Isopropylbenzimidazo[2,1-b]quinazolin-12(6H)one is prepared with benzimidazo[2,1-b]quinazolin-12(6H)one and isopropyl bromide.

3,6,8,9-Tetramethylbenzimidazo[2,1-b]quinazolin-12(6H)-one is prepared with 3,8,9-trimethylbenzimidazo[2,1-b]quinazolin-12(6H)one and methyl iodide.

6-(n-Octyl)benzimidazo[2,1-b]quinazolin-12(6H)one is prepared with benzimidazo[2,1-b]quinazolin-12(6H)one and n-octyl bromide.

6-Methyl-8,9-dichlorobenzimidazo[2,1-b]quinazolin-12(6H)-one is prepared with 8,9-dichlorobenzimidazo[2,1-b]quinazolin-12(6H)one and methyl bromide.

6-(n-Butyl)benzimidazo[2,1-b]quinazolin-12(6H)one is prepared with benzimidazo[2,1-b]quinazolin-12(6H)one and n-butyl bromide.

6-Methyl-3-trifluoromethylbenzimidazo[2,1-b]quinazolin-12(6H)one is prepared with 3-trifluoromethylbenzimidazo[2,1-b]-quinazolin-12(6H)one and methyl iodide.

6-(n-Dodecyl)benzimidazo[2,1-b]quinazolin-12(6H)one is prepared with benzimidazo[2,1-b]quinazolin-12(6H)one and n-dodecyl bromide.

6-(n-Propyl)-3-nitrobenzimidazo[2,1-b]quinazolin-12(6H)-one is prepared with 3-nitrobenzimidazo[2,1-b]quinazolin-12(6H)one and n-propyl bromide.

2-Ethyl-6,8,9-Trimethylbenzimidazo[2,1-b]quinazoline-12(6H)one is prepared with 2-ethyl-8,9-dimethylbenzimidazo[2,1-b]-quinazolin-12(6H)one and methyl bromide.

3,8,9-Trichloro-6-(n-propyl)benzimidazo[2,1-b]quinazolin-12(6H)one is prepared with 3,8,9-trichlorobenzimidazo[2,1-b]-quinazolin-12(6H)one and n-propyl bromide.

3-Bromo-6-(n-hexyl)benzimidazo[2,1-b]quinazolin-12(6H)one is prepared with 3-bromobenzimidazo[2,1-b]quinazolin-12(6H)one and n-hexyl bromide.

3-Ethoxy-6-isobutyl-8,9-dimethylbenzimidazo[2,1-b]-quinazolin-12(6H)one is prepared with 3-ethoxy-8,9-dimethylbenzimidazo[2,1-b]quinazolin-12(6H)one and isobutyl bromide.

6-Allylbenzimidazo[2,1-b]quinazolin-12(6H)one is prepared with benzimidazo[2,1-b]quinazolin-12(6H)one and allyl bromide.

2-Methyl-6-(2-butenyl)benzimidazo[2,1-b]quinazolin-12(6H)one is prepared with 2-methyl-benzimidazo[2,1-b]quinazolin-12(6H)one and 1-bromobutene-2.

3-Chloro-6-(3-pentenyl)-8,9-dimethylbenzimidazo[2,1-b]-quinazolin-12(6H)one is prepared with 3-chloro-8,9-dimethylbenzimidazo[2,1-b]quinazolin-12(6H)one and 1-bromopentene-3.

6-Benzylbenzimidazo[2,1-b]quinazolin-12(6H)one is prepared with benzimidazo[2,1-b]quinazolin-12(6H)one and benzyl chloride.

EXAMPLE 19

To a vigorously stirred suspension of 1.18 g. of benzimidazo[2,1-b]quinazolin-12(6H)one in 50 ml. of dry dimethylformamide was added 0.23 g. of a suspension of sodium hydride in mineral oil (58.8 percent sodium hydride) and the mixture was stirred at ambient room temperature for 2 hours. Epibromohydrin, 0.9 g. was added and vigorous agitation was continued for 16 hours. The reaction mixture was then poured into ice water with the formation of a white solid precipitate. The precipitate was filtered and crystallized from hot dimethylformamide. Sequential recrystallizations from methylene chloride and acetone yielded 0.35 g. of 6-(2,3-epoxypropyl)benzimidazo[2,1-b]quinazolin-12(6H)one as a white crystalline solid melting at about 210°–212° C. Elemental analysis of a sample of the product after drying at room temperature gave the following results.

Calculated for $C_{17}H_{13}N_3O_2$: C, 70.09; H, 4.50; N, 14.43; O, 10.99. Found: C, 70.16; H, 4.80; N, 14.18; O, 11.03.

In an analogous manner the following compounds are prepared by the reaction of the appropriate benzimidazo[2,1-b]-quinazolin-12(6H)one with the indicated epoxyalkyl halide:

3-Methyl-6-(2,3-epoxybutyl)benzimidazo[2,1-b]quinazolin-12(6H)one is prepared with 3-methyl-benzimidazo[2,1-b]quinazolin-12(6H)one and 1-bromo-2,3-epoxybutane.

3-Chloro-6-(3,4-epoxypentyl)benzimidazo[2,1-b]quinazolin-12(6H)one is prepared with 3-chlorobenzimidazo[2,1-b]quinazolin-12(6H)one and 1-bromo-3,4-epoxypentane.

EXAMPLE 20

To a vigorously stirred suspension of 4.7 g. of benzimidazo[2,1-b]quinazolin-12(6H)one in 130 ml. of dry dimethylformamide was added 1.15 g. of a suspension of sodium hydride in mineral oil (57 percent sodium hydride). Chloromethylmethyl ether, 2 g. in 10 ml. of dry dimethylformamide was added dropwise over 20 minutes and the reaction mixture was stirred overnight at ambient room temperature. The reaction mixture was poured into 400 ml. of ice water and the white solid precipitate which formed was filtered and recrystallized from dimethylformamide to yield 4 g. of 6-methoxymethylbenzimidazo[2,1-b]quinazolin-12(6H)one as a white crystalline solid melting at about 221°–223° C.

In a similar manner, the following compounds can be prepared by employing the appropriate benzimidazo[2,1-b]quinazolin-12(6H)one with the indicated halo ether alkylating agent:

6-Ethoxymethylbenzimidazo[2,1-b]quinazolin-12(6H)one is prepared with benzimidazo[2,1-b]quinazolin-12(6H)one and chloromethylethyl ether.

3,8,9-Trimethyl-6-n-propoxyethylbenzimidazo[2,1-b]-quinazolin-12(6H)one is prepared with 3,8,9-trimethylbenzimidazo[2,1-b]quinazolin-12(6H)one and 2-chloroethylpropyl ether.

3-Chloro-6-n-butoxymethyl-7-nitrobenzimidazo[2,1-b]-quinazolin-12(6H)one is prepared with 3-chloro-7-nitrobenzimidazo[2,1-b]quinazolin-12(6H)one and chloromethyl-n-butyl ether.

EXAMPLE 21

To a vigorously-stirred suspension of 2.36 g. of benzimidazo[2,1-b]quinazolin-12(6H)one in 75 ml. of dry dimethylformamide was added 0.51 g. of a sodium hydride suspension in mineral oil (58.8 percent sodium hydride) and the mixture was stirred at room temperature for 65 hours. Ethyl chloroacetate, 1 ml. was added and the reaction mixture was stirred at ambient room temperature for 24 hours and then poured into 300 ml. of ice water. The white solid precipitate which formed was filtered and recrystallized from dimethylformamide to yield 2.57 g. of ethyl 12(6H)-oxobenzimidazo[2,1-b]quinazolin-6-acetate as white crystalline needles melting at about 238°–240° C.

EXAMPLE 22

To a suspension of 2.36 g. of benzimidazo[2,1-b]quinazolin-12(6H)one in 90 ml. of dry dimethylformamide, 0.46 g. of a sodium hydride mineral oil dispersion containing 57 percent sodium hydride was added with stirring. The mixture was stirred for one half hour and then added dropwise over two hours to a solution of 2.15 g. of methyl 5-bromovalerate in 20 ml. of dry dimethylformamide. The reaction mixture was stirred for two hours longer and then poured into ice water. The solid precipitate which formed was separated and dissolved in benzene, and insoluble impurities were removed by filtration. The precipitate was dried by evaporation of a benzene water azeotrope. Crystallization of the precipitate from acetone-benzene yielded 2.17 g. of 6-(4-carbomethoxybutyl)-benzimidazo[2,1-b]quinazolin-12(6H)one as a white crystalline solid melting at about 130°–132° C.

In an analogous manner, the following compounds are prepared by the reaction of the appropriate benzimidazo[2,1-b]quinazolin-12(6H)one with the designated halo carboxylic acid or ester:

6-(Carboethoxymethyl)-3-methylbenzimidazo[2,1-b]-quinazolin-12(6H)one is prepared with 3-methylbenzimidazo[2,1-b]quinazoline-12(6H)one and ethyl bromoacetate.

6-(Carbomethoxyethyl)-3-methyl-8,9-dichlorobenzimidazo-[2,1-b]quinazolin-12(6H)one is prepared with 3-methyl-8,9-dichlorobenzimidazo[2,1-b]quinazolin-12(6H)one and methyl 3-chloropropionate.

6-(Carboethoxypropyl)-3-methyl-9-ethoxybenzimidazo[2,1-b]quinazolin-12(6H)one is prepared with 3-methyl-9-ethoxybenzimidazo[2,1-b]quinazolin-12(6H)one and ethyl 4-bromobutyrate.

EXAMPLE 23

To a well-stirred suspension of 5.89 g. of benzimidazo-[2,1-b]quinazolin-12(6H)one in 150 ml. of dry dimethylformamide were added 1.21 g. of a sodium hydride dispersion in mineral oil containing 57 percent sodium hydride, and stirring continued for 1 hour. The resulting mixture was then added dropwise over 3 hours to a stirred solution of 4.75 g. of methyl 4-oxo-5-chlorovalerate in 40 ml. of dry dimethylformamide. The reaction mixture was stirred for two hours at ambient room temperature and then poured into ice water. The white solid precipitate which formed was filtered and air dried. Consecutive crystallizations of the precipitate from dimethylformamide, chloroform acetonitrile and, finally, acetonitrile yielded 1.67 g. of 6-(4-carbomethoxy-2-oxobutyl)benzimidazo[2,1-b]quinazolin-12(6H)one as a crystalline solid melting at about 199°–201° C.

In an analogous manner, the following compounds can be prepared with the appropriate benzimidazo[2,1-b]quinazolin-12(6H)one and the designated ketoacid ester:

6-(4-Carbomethoxy-3-oxobutyl)-2-methyl-8,9-dichlorobenzimidazo[2,1-b]quinazolin-12(6H)one if prepared with 2 methyl-8,9-dichlorobenzimidazo[2,1-b]quinazolin-12(6H)one and methyl 3-oxo-5-chlorovalerate.

6-(3-Carboethoxy-2-oxopropyl)-4-nitro-8,9-dimethylbenzimidazo[2,1-b]quinazolin-12(6H)one is prepared with 4-nitro-8,9-dimethylbenzimidazo[2,1-b]quinazolin-12(6H)one and ethyl 3-oxo-4-chlorobutyrate.

EXAMPLE 24

A dispersion of sodium hydride in mineral oil, 1.07 g. containing 57 percent sodium hydride, was added to a vigorously stirred mixture of 4.7 g. of benzimidazo[2,1-b]quinazolin-12(6H)one in 130 ml. of dry dimethylformamide and stirring was continued until complete solution was attained. A solution of 3.16 g. of 3-chlorodimethylaminopropane in 10 ml. of dry dimethylformamide was added dropwise over 25 minutes with continued stirring. The reaction mixture was stirred for 1 hour at room temperature and then heated to a temperature of 100° C. for 2 hours. On cooling, the reaction mixture was poured into ice water, yielding a gummy, semi-solid precipitate. The precipitate solidified upon the addition of a small volume of acetone. The precipitate was filtered, dried, and recrystallized from acetone four times to yield 1.06 g. of substantially pure 6-(3-dimethylamino-n-propyl)-benzimidazo[2,1-b]quinazolin-12(6H)one melting at about 164°–165° C.

In an analogous manner, the following compounds can be prepared with the designated benzimidazo[2,1-b]quinazolinone and dialkylaminoalkyl halide:

6-(2-Dimethylaminoethyl)-4-chlorobenzimidazo[2,1-b]-quinazolin-12(6H)one is prepared with 4-chlorobenzimidazo[2,1-b]-quinazolin-12(6H)one and 2-chlorodimethylaminoethane.

6-(4-Diethylamino-n-butyl)-3,8,9-trimethylbenzimidazo[2,1-b]quinazolin-12(6H)one is prepared with 3,8,9-trimethylbenzimidazo[2,1-b]quinazolin-12(6H)one and 4-bromodiethylaminobutane.

6-(2-di(n-Propyl)aminoethyl)-3-methoxybenzimidazo[2,1-b]-quinazolin-12(6H)one is prepared with 3-methoxybenzimidazo[2,1-b]-quinazolin-12(6H)one and 2-chlorodi(n-propyl)aminoethane.

EXAMPLE 25

Benzimidazo[2,1-b]quinazolin-12(6H)one, 4.7 g., was converted to the sodium salt with sodium hydride in 180 ml. of dry dimethylformamide and 5.18 g. of phenacyl bromide was added with vigorous agitation. The reaction mixture was stirred overnight and poured into ice water. The solid which separated was filtered, dried, and recrystallized from dimethylformamide to yield 4.2 g. of 6-phenacylbenzimidazo[2,1-b]quinazolin-12(6H)one melting with decomposition at about 200° C.

In like manner, the following compounds can be prepared by employing the designated starting materials:

6-(4-Methylphenacyl)-8,9-dimethylbenzimidazo[2,1-b]-quinazolin-12(6H)one is prepared with 8,9-dimethylbenzimidazo-[2,1-b]quinazolin-12(6H)one and 4-methylphenacyl bromide.

6-[β-(4-Methoxybenzoyl)ethyl]-2-chlorobenzimidazo[2,1-b]-quinazolin-12(6H)one is prepared with 2-chlorobenzimidazo[2,1-b]-quinazolin-12(6H)one and 2-(4-methoxybenzoyl)ethyl bromide.

6-[4-(4-Chlorobenzoyl)butyl]-2-methyl-8,9-dichlorobenzimidazo[2,1-b]quinazolin-12(6H)one is prepared with 2-methyl-8,9-dichlorobenzimidazo[2,1-b]quinazolin-12(6H)one and 4-(4-chlorobenzoyl)butyl bromide.

EXAMPLE 26

Benzimidazo[2,1-b]quinazolin-12(6H)one, 7.05 g. in 200 ml. of dry dimethylformamide was converted to the sodium derivative with sodium hydride according to the procedures described in previous examples, and 2,4-dimethylbenzoyl chloride, 5.8 g. in 25 ml. of dimethylformamide were added dropwise with vigorous stirring. The reaction mixture was stirred for an additional hour and then poured into ice water. The precipitate which formed was filtered, washed with water, dried and twice recrystallized from benzene to yield 6-(2,4-dimethylbenzoyl)benzimidazo[2,1-b]quinazolin-12(6H)one as a crystalline solid melting at about 213°-214° C.

In a similar manner, the following compounds are prepared by the reaction of the designated starting materials:

6-Acetyl-3-chlorobenzimidazo[2,1-b]quinazolin-12(6H)one is prepared with 3-chlorobenzimidazo[2,1-b]quinazolin-12(6H)one and acetyl chloride.

6-Propionyl-3-methylbenzimidazo[2,1-b]quinazolin-12(6H)one is prepared with 3-methylbenzimidazo[2,1-b]quinazolin-12(6H)one and propionyl chloride.

6-Palmitoyl-8,9-dimethylbenzimidazo[2,1-b]quinazolin-12(6H)one is prepared with 8,9-benzimidazo[2,1-b]quinazolin-12(6H)one and palmitoyl chloride.

6-Cyclopentanoyl-2-chlorobenzimidazo[2,1-b]quinazolin-12(6H)one is prepared with 2-chlorobenzimidazo[2,1-b]quinazolin-12(6H)one and cyclopentanoyl chloride.

6-(4-Methylcyclohexanoyl)benzimidazo[2,1-b]quinazolin-12(6H)one is prepared with benzimidazo[2,1-b]quinazolin-12(6H)one and 4-methylcyclohexanoyl chloride.

6-(3-Methylcyclooctanoyl)benzimidazo[2,1-b]quinazolin-12(6H)one is prepared with benzimidazo[2,1-b]quinazolin-12(6H)one and 3-methylcyclooctanoyl chloride.

6-(Bicyclo[2.2.1]heptanoyl)benzimidazo[2,1-b]quinazolin-12(6H)one is prepared with benzimidazo[2,1-b]quinazolin-12(6H)one and bicyclo[2.2.1]heptanoyl bromide.

6-(1,7,7-Trimethylbicyclo[2.2.1]heptanoyl)-2-methylbenzimidazo[2,1-b]quinazolin-12(6H)one is prepared with 2-methylbenzimidazo[2,1-b]quinazolin-12(6H)one and 1,7,7-trimethylbicyclo[2.2.1]heptanoyl chloride.

6-(Bicyclo[3.3.0]octenoyl)-3-nitrobenzimidazo[2,1-b]-quinazolin-12(6H)one is prepared with 3-nitrobenzimidazo[2,1-b]-quinazolin-12(6H)one and bicyclo[3.3.0]octenoyl bromide.

6-(5-Methylbicyclo[5.3.0]cyclodecenoyl)benzimidazo[2,1-b]-quinazolin-12(6H)one is prepared with benzamidazo[2,1-b]quinazolin-12(6H)one and 5-methylbicyclo[5.3.0]cyclodecenoyl chloride.

6-Benzoyl-3-methyl-8,9-dichlorobenzimidazo[2,1-b]-quinazolin-12(6H)one is prepared with 3-methyl-8,9-dichlorobenzimidazo[2,1-b]quinazolin-12(6H)one and benzoyl chloride.

6-(3,5-Dimethylbenzoyl)-3-methoxybenzimidazo[2,1-b]-quinazolin-12(6H)one is prepared with 3-methoxybenzimidazo[2,1-b]quinazolin-12(6H)one and 3,5-dimethylbenzoyl chloride.

6-(2,4-Dichlorobenzoyl)-9-ethoxybenzimidazo[2,1-b]-quinazolin-12(6H)one is prepared with 9-ethoxybenzimidazo[2,1-b]-quinazolin-12(6H)one and 2,4-dichlorobenzoyl chloride.

6-(2-Carbomethoxybenzoyl)-2-bromobenzimidazo[2,1-b]quinazolin-12(6H)one is prepared with 2-bromobenzimidazo[2,1-b]quinazolin-12(6H)one and 2-carbomethoxybenzoylchloride.

6-(4-Isopropoxybenzoyl)-3,8,9-trimethylbenzimidazo[2,1-b]-quinazolin-12(6H)one is prepared with 3,8,9-trimethylbenzimidazo[2,1-b]quinazolin-12(6H)one and 4-isopropoxybenzoyl chloride.

EXAMPLE 27

Benzimidazo[2,1-b]quinazolin-12(6H)one, 3.54 g., in 100 ml. of dry dimethylformamide was converted to the sodium derivative with sodium hydride according to the procedures described in previous examples, and the sodium derivative was slowly added with stirring to 3.3 g. of methyl 4-(chloroformyl)butyrate dissolved in 50 ml. of anhydrous dimethylformamide. The reaction mixture was stirred at ambient temperature for 24 hours and then poured into 400 ml. of ice water. The precipitate which formed was filtered, dried and recrystallized from chloroform to yield 2.41 g. of the product, 6-(4-Carbomethoxybutyryl)benzimidazo[2,1-b]quinazolin-12(6H)one as a white crystalline solid melting at about 159.5°-161° C.

In an analogous manner, the following compounds are prepared by the reaction of the appropriately substitued benzimidazo[2,1-b]quinazolin with the designated half acid ester acyl chloride of a dibasic acid:

6-(3-Carbomethoxypropionyl)benzimidazo[2,1-b]quinazolin-12(6H)one is prepared with benzimidazo[2,1-b]quinazolin-12(6H)one and methyl 3-(chloroformyl)propionate.

6-(6-Carboethoxyhexanoyl)benzimidazo[2,1-b]quinazolin-12(6H)one is prepared with benzimidazo[2,1-b]quinazolin-12(6H)one and ethyl 6-(chloroformyl)hexanoate.

6-(5-Carbomethoxypentanoyl)-3-methylbenzimidazo[2,1-b]-quinazolin-12(6H)one is prepared with 3-methylbenzimidazo[2,1-b]-quinazolin-12(6H)one and methyl 5-(chloroformyl)pentanoate.

EXAMPLE 28

Benzimidazo[2,1-b]quinazolin-12(6H)one, 7.05 g. (30 mmole) was stirred in 200 ml. of dry tetrahydrofuran and 1.63 g. of a suspension of sodium hydride in mineral oil (containing 58 percent sodium hydride) was added. Stirring was continued until hydrogen evolution ceased.

2,4,6-Trimethylbenzoyl chloride, 6.57 g. (36 mmole) in 25 ml. of dry dimethylformamide was added dropwise with stirring and the mixture was stirred for 16 hours, during which time the yellow color disappeared. The whole was then poured into ice water and the solid was collected by filtration, washed with water, dried and recrystallized from acetonitrile to yield 6-(2,4,6-trimethylbenzoyl)benzimidazo[2,1-b]quinazolin-12(6H)one.

I claim:

1. The method for suppressing the immune reaction in a mammal which comprises administering parenterally to said mammal an effective dose between about 0.1 to about 100 mg./kg. of body weight of a compound of the formula:

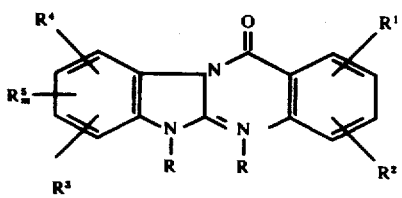

wherein $R^1$, $R^2$, $R^3$ and $R^4$ when taken separately are hydrogen, $C_1$ to $C_4$ lower alkyl, $C_1$ to $C_4$ lower alkoxy, halogen, nitro, amino, carb-($C_1$-$C_4$)alkoxy, or trifluoromethyl, and $R^1$ and $R^2$ or $R^3$ and $R^4$ when taken together with the adjacent ring carbon atoms to which they are attached form a six-membered aromatic carbocyclic ring; $R^5$ is methyl or chloro; and m is an integer of from 0 to 2, with the limitation that when $R^3$ and $R^4$ are other than methyl or chloro, m is 0; and wherein R is hydrogen, $C_1$ to $C_{12}$ alkyl, $C_3$ to $C_5$ alkenyl, $C_3$ to $C_5$ epoxyalkyl, $C_2$ to $C_{16}$ alkanoyl, benzyl, $C_4$ to $C_{11}$ cycloalkanoyl, $C_8$ to $C_{13}$ bicycloalkanoyl, $C_8$ to $C_{13}$ bicycloalkenoyl, or -[$CH_2$]$_p$-Z, wherein p is an integer of from 1 to 4 and Z is lower alkoxy, carboxy, carb-$C_1$-$C_4$alkoxy, di-lower alkylamino, or a group of the formula

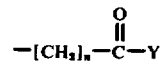

wherein n is an integer of from 0 to 4 and Y is carboxy lower alkyl, carb-($C_1$-$C_4$)alkoxy lower alkyl, phenyl, naphthyl, phenyl substituted by lower alkyl, lower alkoxy, halogen, nitro, amino, carboxy or carb-($C_1$-$C_4$)alkoxy, or naphthyl substituted by lower alkoxy, halogen, nitro, amino, carboxy or carb-($C_1$-$C_4$)alkoxy, with the limitation that when Y is carboxy lower alkyl or carb-($C_1$-$C_4$)alkoxy lower alkyl, n is 0 or 1, and when Y is naphthyl or substituted naphthyl, n is 0.

2. The method according to claim 1 wherein 6-methylbenzimidazo[2,1-b]quinazolin-12(6H)one is administered.

3. The method according to claim 1 wherein 8,9-dimethylbenzimidazo[2,1-b]quinazolin-12(6H)one is administered.

4. The method according to claim 1 wherein 3-methylbenzimidazo[2,1-b]quinazolin-12(6H)one is administered.

5. The method according to claim 1 wherein 6-benzoylbenzimidazo[2,1-b]quinazolin-12(6H)one is administered.

6. The method according to claim 1 wherein naphth-[2', 3':5,6]pyrimidazo[3,2-a]benzimidazo-13(5H)one is administered.

* * * * *